United States Patent
Hanan

(10) Patent No.: US 8,308,636 B2
(45) Date of Patent: Nov. 13, 2012

(54) DEVICE FOR A RECTOSCOPE

(75) Inventor: Manan Hanan, Sandnes (NO)

(73) Assignee: Olav Hovda (NO)

( * ) Notice: Subject to any disclaimer, the term of this patent is extended or adjusted under 35 U.S.C. 154(b) by 442 days.

(21) Appl. No.: 12/601,194

(22) PCT Filed: May 21, 2008

(86) PCT No.: PCT/NO2008/000176
§ 371 (c)(1),
(2), (4) Date: Apr. 12, 2010

(87) PCT Pub. No.: WO2008/143521
PCT Pub. Date: Nov. 27, 2008

(65) Prior Publication Data
US 2010/0191059 A1    Jul. 29, 2010

(30) Foreign Application Priority Data
May 23, 2007  (NO) .................................. 20072648

(51) Int. Cl.
*A61B 1/12*  (2006.01)
(52) U.S. Cl. ........................................................ 600/156
(58) Field of Classification Search ........... 600/156–158
See application file for complete search history.

(56) References Cited

U.S. PATENT DOCUMENTS

| | | | | |
|---|---|---|---|---|
| 2,767,705 | A | * | 10/1956 | Moore ........................ 600/184 |
| 4,538,594 | A | | 9/1985 | Boebel et al. |
| 6,110,103 | A | | 8/2000 | Donofrio |
| 6,585,642 | B2 | * | 7/2003 | Christopher ................. 600/156 |
| 7,150,713 | B2 | * | 12/2006 | Shener et al. ................ 600/156 |
| 2001/0056222 | A1 | | 12/2001 | Rudischhauser et al. |
| 2003/0032860 | A1 | | 2/2003 | Avni et al. |
| 2006/0069306 | A1 | | 3/2006 | Banik et al. |
| 2010/0191059 | A1 | * | 7/2010 | Hanan ........................ 600/156 |

FOREIGN PATENT DOCUMENTS

| | | |
|---|---|---|
| DE | 4404253 A1 | 8/1995 |
| GB | 1 405 025 A | 9/1975 |
| WO | 00/48505 A1 | 8/2000 |

OTHER PUBLICATIONS

International Search Report for parent application PCT/NO2008/000176, having a mailing date of Sep. 4, 2008.

* cited by examiner

*Primary Examiner* — W. B. Perkey
(74) *Attorney, Agent, or Firm* — Andrus, Sceales, Starke & Sawall, LLP

(57) ABSTRACT

A device for a rectoscope including a main pipe which is provided, at a first end portion, with a connection sub arranged to receive an optics head, and an elongated insertion portion, a second end portion being provided with a rectoscope mouth, and the center bore of the main pipe being arranged to receive an insertion cone, at least one fluid line being arranged in the main pipe, the fluid line extending from the first end portion to a second end portion of the main pipe.

9 Claims, 2 Drawing Sheets

DEVICE FOR A RECTOSCOPE

CROSS-REFERENCE TO RELATED APPLICATIONS

This application is the U.S. national stage application of International Application No. PCT/NO2008/000176, filed May 21, 2008, which International application was published on Nov. 27, 2008, as International Publication No. WO 2008/143521 A1 in the English language, which application is incorporated herein by reference. The International application claims priority of Norwegian Patent Application No. 20072648, filed May 23, 2007, which application is incorporated herein by reference.

BACKGROUND

The invention relates to a device for a rectoscope, more particularly, a rectoscope arranged for connection to a standardized optics head for the illumination and viewing of a rectal area, and a suction device for use in the removal of rectal contents during the examination, the rectoscope being provided with a manoeuvrable suction tip arranged at one end portion of the rectoscope and arranged to be in an operative position during the phase in which the rectoscope is moved in the area of examination while this is dilated by means of a fluid, preferably air, under overpressure.

When a prior art rectoscope, for example a Welch Allyn No. 53130, is used for the visual examination of the rectum and possibly sampling, the rectoscope is moved in the portion of the rectum to be examined, while the rectum is kept dilated by a supply of fluid, normally air, at a certain overpressure, and the person who is performing the examination, observes the condition of the rectum, after an enema, via appropriate equipment, for example an optics head of the Heine E7 type. When there is a need to remove liquid, for example intestinal fluid or blood, for a better visual view of the area to be examined, the rectoscope needs to be opened for the insertion of a suction pipe, for example an Astra Tech Medena M0600, which is connected to a suction pump device via appropriate hoses. As the rectoscope is opened, air leaks out, and the view is reduced. The connection, insertion and removal of the suction pipe takes time and entails increased discomfort for the patient, especially by repeated inflation (ballooning) of the rectum, the medical personnel loses track of the situation as the possibility of a continuous visual inspection of the rectal area is prevented, and storage of the suction pipe outside the rectoscope between each suction operation involves a hygienic disadvantage.

In itself, a rectoscopy often represents great emotional stress to the patient, as the intimacy of the patient is affected, and the patient is in a psychologically uncomfortable, highly undesired, to some extent enforced, but necessary situation, and there is a strong need to make this situation as short-lasting and physically comfortable as possible.

SUMMARY

The invention has for its object to remedy or reduce at least one of the drawbacks of the prior art.

The object is achieved through features which are specified in the description below and in the claims that follow.

The object of the present invention is to provide a rectoscope which also includes, in addition to the known features providing connection to necessary equipment and enabling visual inspection of the area to be examined, ballooning of the rectum and possible sampling (biopsy), at least one integrated fluid line which is in an operative position within the rectoscope during the entire examination, the rectoscope according to the invention enabling suction while the rectum is ballooned and in a viewable state. The rectoscope according to the invention preferably also includes the possibility of controlled rinsing of the rectum under full visual view, either by the rinsing being carried out through said fluid line arranged for suction, or by the arrangement of at least one second fluid line arranged to supply a rinsing fluid, for example water, to the area under examination. The characteristics of the present invention make it possible to perform a rectoscopy with a greater degree of precision than with the use of the prior art, as the necessary rinsing and suction of liquid and particles can be carried out under continuous visual monitoring of the ballooned area of the rectum through the optics head of the rectoscope, and without the need to carry out repeated supplementing with air for the ballooning to be maintained.

Thereby, the invention results in a better quality of the rectoscopy, reduced time consumption and reduced costs for the examination, and in addition the patient's physical and psychological discomfort by the examination is mitigated.

More specifically, the invention relates to a device for a rectoscope including a main pipe which is provided, in a first end portion, with a connection sub which is arranged to receive an optics head, an elongated insertion portion, a second end portion thereof being provided with a rectoscope mouth, the centre bore of the main pipe being arranged to receive an insertion cone, characterized by at least one fluid line being arranged in the main pipe, the fluid line extending from the first end portion to a second end portion of the main pipe.

The fluid line is preferably formed as a fluid pipe arranged at the periphery of the centre bore and secured to the main pipe. Alternatively, the fluid line is formed as a channel embedded in the wall of the main pipe.

The fluid line preferably includes a first end portion forming a fluid line mouth arranged adjacent to the periphery of the rectoscope mouth.

It is an advantage that the fluid line mouth is flush with the end of the rectoscope mouth.

The fluid line preferably includes a second end portion which is arranged to be connected to a fluid plant.

The second end portion of the fluid line preferably projects from the periphery of the main pipe. Alternatively, the second end portion of the fluid line is arranged to be connected to the fluid plant via a connection to the optics head.

The fluid plant is advantageously arranged to provide a controlled underpressure at the fluid line mouth. Alternatively, the fluid plant is also arranged to provide a liquid flow through the fluid line and out through the fluid line mouth.

The insertion cone is preferably provided with a peripheral recess arranged to accommodate a portion of the fluid line.

BRIEF DESCRIPTION OF THE DRAWINGS

In what follows is described an example of a preferred embodiment which is visualized in the accompanying drawings, in which.

DETAILED DESCRIPTION OF THE DRAWINGS

Figure 1:
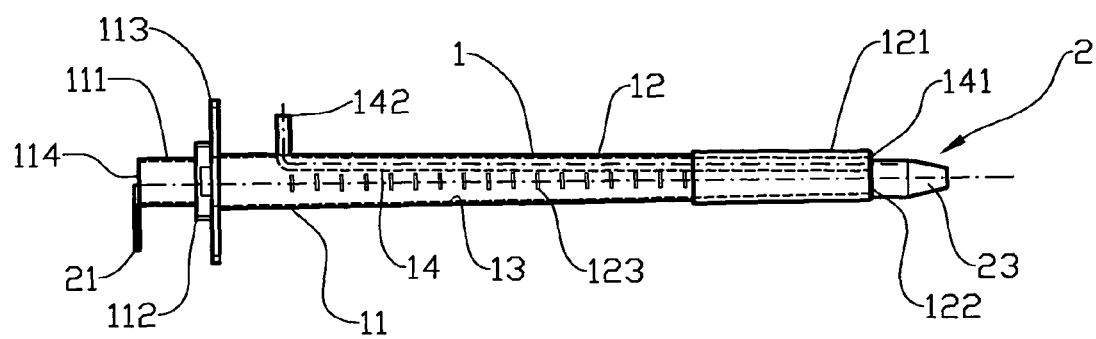
FIG. 1 shows a side view of the rectoscope according to the invention.
Figure 2:
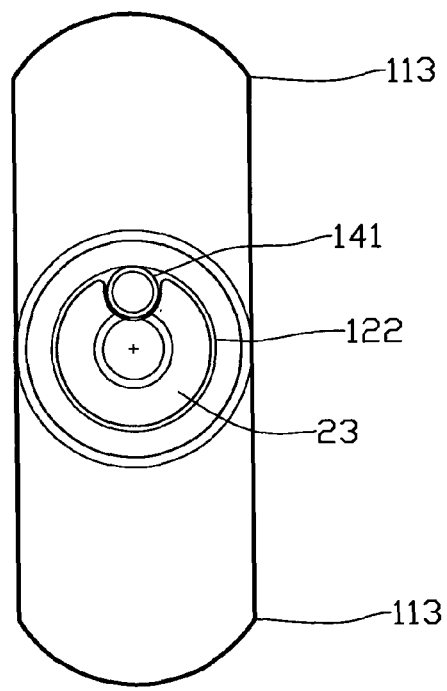
FIG. 2 shows, on a larger scale, an end view of the rectoscope seen from the insertion end.
Figure 3:
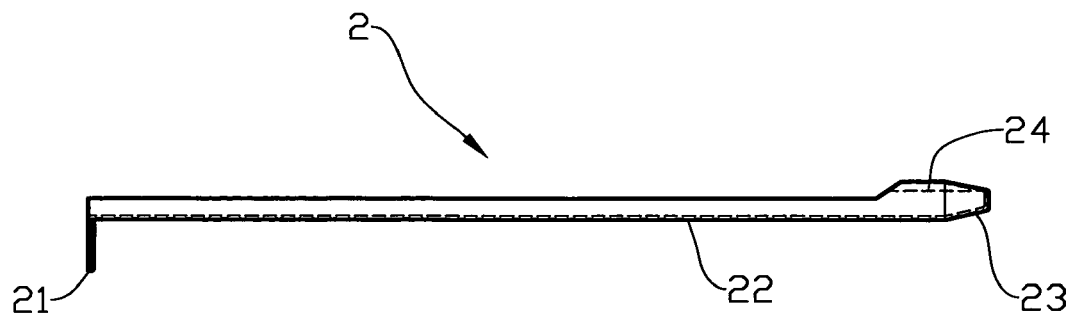
FIG. 3 shows a side view of an insertion cone on the same scale as FIG. 1.
Figure 4:
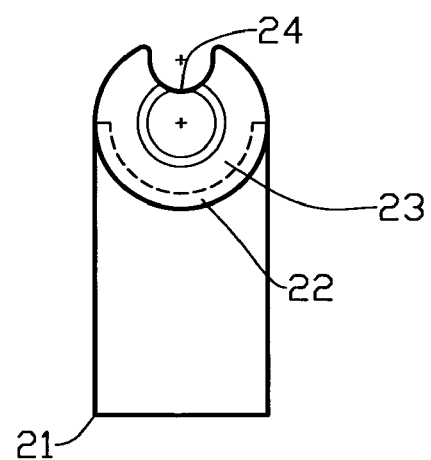
FIG. 4 shows an end view of the insertion cone on the same scale as FIG. 3.

A rectoscope according to the invention is provided with a cylindrical main pipe 1, in which a first end portion 11 is provided with a detachable connection sub 111, standardized connection details 112 for the releasable connection of the rectoscope to a prior art optics head (not shown) known per se, and two radially projecting grips 113 arranged to form natural gripping surfaces for an operator during the use of the rectoscope. The connection sub 111 forms a rectoscope entrance 114.

An elongated insertion portion 12 is provided with a second end portion 121 exhibiting a larger diameter than the rest of the insertion portion 12. The end portion 121 is provided with a substantially circular rectoscope mouth 122. A centre bore 13 extends continuously through the entire rectoscope from the first end portion 11 to the rectoscope mouth 122.

The centre bore 13 is arranged to receive an insertion cone 2. The insertion cone 2 is provided with a handle 21, a shaft 22 and a cone end portion 23 and is arranged to be inserted into the centre bore 13 through the rectoscope entrance 114 and with the cone end portion 23 first until the cone end portion 23 projects from the rectoscope mouth 122 and the handle 21 hits the connection sub 111.

The insertion portion 12 is provided with a length scale 123 indicating, with reference to the rectoscope mouth 122, a reference of how far the rectoscope has been inserted into an area of examination (not shown).

A fluid line 14 is arranged in the periphery of the centre bore 13 parallel to the centre axis of the rectoscope and in a substantial part of the longitudinal extent of the rectoscope. The fluid line 14 extends from the rectoscope mouth 122, where a fluid line mouth 141 is flush with the rectoscope mouth 122 and is secured at the periphery of the rectoscope mouth 122 and at the periphery of the centre bore 13 at least at points in a substantial part of the extent of the fluid line 14. A second end portion 142 of the fluid line 14 is bent and projects radially from the rectoscope in the first end portion 11 of the rectoscope and is arranged for releasable connection to a fluid plant (not shown) via a flexible conduit (not shown).

The cone end portion 23 of the insertion cone 2 exhibits a recess 24 which is complementary to the fluid line 14 and encloses a substantial part of the fluid line mouth 141 but allows the insertion cone 2 to be freely inserted through the centre bore 13.

When a rectoscopy is to be performed with the rectoscope according to the invention, the insertion cone 2 is positioned in the centre bore 13, and lubricants are applied to the insertion portion 12 and cone end portion 23 in accordance with a technique known per se to facilitate the insertion into the rectum.

Once the rectoscope has been inserted sufficiently far with reference to the length scale 123, the insertion cone 2 is pulled out, and the prior art optics head (not shown) known per se is connected to the connection sub 111 of the rectoscope and locked to the connection details 112. The ballooning means of the optics head are operated so that the rectum is ballooned (inflated) while the operator is viewing the rectal portion through the optics.

When particles and/or liquid make(s) visual examination of the rectum difficult, the fluid plant (not shown) connected to the second end portion 142 of the fluid line 14 is used and rinsing or suction is enabled as required. Through the axial and rotational movement of the rectoscope, the fluid line mouth 141 is carried towards the area to be rinsed/sucked, and the fluid plant is operated under continuous monitoring via the optics head.

The invention claimed is:

1. A device for a rectoscope comprising a main pipe (1) which is provided, at a first end portion (11), with a connection sub (111) arranged for releasable connection to an optics head, an insertion cone (2) and an elongated insertion portion (12), a second end portion (121) being provided with a rectoscope mouth (122), and the centre bore (13) of the main pipe (1) being arranged to receive the insertion cone (2), characterized in that at least one fluid line (14) is arranged in the main pipe (1), the fluid line (14) extending from the first end portion (11) to a second end portion (121) of the main pipe (1); and the fluid line (14) is arranged as a fluid pipe arranged at the periphery of the centre bore (13) and secured to the main pipe (1), or as a channel embedded in the wall of the main pipe (1).

2. The device in accordance with claim 1, characterized in that the fluid line (14) comprises a first end portion which forms a fluid line mouth (141) arranged adjacent to the periphery of the rectoscope mouth (122).

3. The device in accordance with claim 2, characterized in that the fluid line mouth (141) is flush with the end of the rectoscope mouth (122).

4. The device in accordance with claim 1, characterized in that the fluid line (14) includes a second end portion (142) which is arranged to be connected to a fluid plant.

5. The device in accordance with claim 4, characterized in that the second end portion (142) of the fluid line (14) projects from the periphery of the main pipe (1).

6. The device in accordance with claim 4, characterized in that the second end portion (142) of the fluid line (14) is arranged to be connected to the fluid plant by connection to the optics head.

7. The device in accordance with claim 4, characterized in that the fluid plant is arranged to provide a controlled underpressure at the fluid line mouth (141).

8. The device in accordance with claim 4, characterized in that the fluid plant is arranged to provide a liquid flow through the fluid line (14) and out through the fluid line mouth (141).

9. The device in accordance with claim 1, characterized in that the insertion cone (2) is provided with a peripheral recess (24) arranged to accommodate a portion of the fluid line (14).

* * * * *

UNITED STATES PATENT AND TRADEMARK OFFICE
CERTIFICATE OF CORRECTION

PATENT NO. : 8,308,636 B2
APPLICATION NO. : 12/601194
DATED : November 13, 2012
INVENTOR(S) : Manan Hanan It is certified that error appears in the above-identified patent and that said Letters Patent is hereby corrected as shown below:

Please replace the listing of claims at column 4, lines 14-55 with the following listing:

--1. A device for a rectoscope comprising a main pipe which is provided, at a first end portion, with a connection sub arranged for releasable connection to an optics head, an insertion cone and an elongated insertion portion, a second end portion being provided with a rectoscope mouth, and the centre bore of the main pipe being arranged to receive the insertion cone, and at least one fluid line is arranged in the main pipe, the fluid line extending from the first end portion to a second end portion of the main pipe, wherein
    the fluid line is arranged as a fluid pipe arranged at the periphery of the centre bore and secured to the main pipe;
    the fluid line comprises a first end portion which forms a fluid line mouth arranged adjacent to the periphery of the rectoscope mouth, the fluid line mouth being flush with the end of the rectoscope mouth; and
    the second end portion of the main pipe forming a mouth being arranged to allow a cone end portion of the insertion cone project from the rectoscope mouth, the insertion cone being provided with a peripheral recess arranged to accommodate a portion of the fluid line.

2. The device in accordance with claim 1, wherein the insertion cone comprises means which by interaction with the first end portion of the main pipe is arranged to limit the cone end portion's projection from the rectoscope mouth.

3. The device in accordance with claim 1, wherein the fluid line includes a second end portion which is arranged to be connected to a fluid plant.

4. The device in accordance with claim 3, wherein the second end portion of the fluid line projects from the periphery of the main pipe.

5. The device in accordance with claim 3, wherein the second end portion of the fluid line is arranged to be connected to the fluid plant by connection to the optics head.

Signed and Sealed this
Ninth Day of April, 2013

Teresa Stanek Rea
*Acting Director of the United States Patent and Trademark Office*

6. The device in accordance with claim 3, wherein the fluid plant is arranged to provide a controlled underpressure at the fluid line mouth.

7. The device in accordance with claim 3, wherein the fluid plant is arranged to provide a liquid flow through the fluid line and out through the fluid line mouth.--

UNITED STATES PATENT AND TRADEMARK OFFICE
CERTIFICATE OF CORRECTION

PATENT NO. : 8,308,636 B2
APPLICATION NO. : 12/601194
DATED : November 13, 2012
INVENTOR(S) : Manan Hanan It is certified that error appears in the above-identified patent and that said Letters Patent is hereby corrected as shown below:

Delete the title page and substitute therefore the attached title page showing the corrected number of claims in patent.

In the claims:

Please replace the listing of claims at column 4, lines 14-55 with the following listing:

--1. A device for a rectoscope comprising a main pipe which is provided, at a first end portion, with a connection sub arranged for releasable connection to an optics head, an insertion cone and an elongated insertion portion, a second end portion being provided with a rectoscope mouth, and the centre bore of the main pipe being arranged to receive the insertion cone, and at least one fluid line is arranged in the main pipe, the fluid line extending from the first end portion to a second end portion of the main pipe, wherein
    the fluid line is arranged as a fluid pipe arranged at the periphery of the centre bore and secured to the main pipe;
    the fluid line comprises a first end portion which forms a fluid line mouth arranged adjacent to the periphery of the rectoscope mouth, the fluid line mouth being flush with the end of the rectoscope mouth; and
    the second end portion of the main pipe forming a mouth being arranged to allow a cone end portion of the insertion cone project from the rectoscope mouth, the insertion cone being provided with a peripheral recess arranged to accommodate a portion of the fluid line.

2. The device in accordance with claim 1, wherein the insertion cone comprises means which by interaction with the first end portion of the main pipe is arranged to limit the cone end portion's projection from the rectoscope mouth.

This certificate supersedes the Certificate of Correction issued April 9, 2013.

Signed and Sealed this
Thirtieth Day of April, 2013

Teresa Stanek Rea
*Acting Director of the United States Patent and Trademark Office*

3. The device in accordance with claim 1, wherein the fluid line includes a second end portion which is arranged to be connected to a fluid plant.

4. The device in accordance with claim 3, wherein the second end portion of the fluid line projects from the periphery of the main pipe.

5. The device in accordance with claim 3, wherein the second end portion of the fluid line is arranged to be connected to the fluid plant by connection to the optics head.

6. The device in accordance with claim 3, wherein the fluid plant is arranged to provide a controlled underpressure at the fluid line mouth.

7. The device in accordance with claim 3, wherein the fluid plant is arranged to provide a liquid flow through the fluid line and out through the fluid line mouth.--

CERTIFICATE OF CORRECTION (continued)

(12) United States Patent
Hanan

(10) Patent No.: US 8,308,636 B2
(45) Date of Patent: Nov. 13, 2012

(54) DEVICE FOR A RECTOSCOPE

(75) Inventor: Manan Hanan, Sandnes (NO)

(73) Assignee: Olav Hovda (NO)

( * ) Notice: Subject to any disclaimer, the term of this patent is extended or adjusted under 35 U.S.C. 154(b) by 442 days.

(21) Appl. No.: 12/601,194

(22) PCT Filed: May 21, 2008

(86) PCT No.: PCT/NO2008/000176
§ 371 (c)(1),
(2), (4) Date: Apr. 12, 2010

(87) PCT Pub. No.: WO2008/143521
PCT Pub. Date: Nov. 27, 2008

(65) Prior Publication Data
US 2010/0191059 A1     Jul. 29, 2010

(30) Foreign Application Priority Data
May 23, 2007   (NO) ................................. 20072648

(51) Int. Cl.
*A61B 1/12*     (2006.01)

(52) U.S. Cl. ........................................................ 600/156

(58) Field of Classification Search .......... 600/156–158
See application file for complete search history.

(56) References Cited

U.S. PATENT DOCUMENTS

| | | | |
|---|---|---|---|
| 2,767,705 A * | 10/1956 | Moore | 600/184 |
| 4,538,594 A | 9/1985 | Boebel et al. | |
| 6,110,103 A | 8/2000 | Donofrio | |
| 6,585,642 B2 * | 7/2003 | Christopher | 600/156 |
| 7,150,713 B2 * | 12/2006 | Shener et al. | 600/156 |
| 2001/0056222 A1 | 12/2001 | Rudischhauser et al. | |
| 2003/0032860 A1 | 2/2003 | Avni et al. | |
| 2006/0069306 A1 | 3/2006 | Banik et al. | |
| 2010/0191059 A1 * | 7/2010 | Hanan | 600/156 |

FOREIGN PATENT DOCUMENTS

| | | |
|---|---|---|
| DE | 4404253 A1 | 8/1995 |
| GB | 1 405 025 A | 9/1975 |
| WO | 00/48505 A1 | 8/2000 |

OTHER PUBLICATIONS

International Search Report for parent application PCT/NO2008/000176, having a mailing date of Sep. 4, 2008.

* cited by examiner

*Primary Examiner* — W. B. Perkey
(74) *Attorney, Agent, or Firm* — Andrus, Sceales, Starke & Sawall, LLP

(57) ABSTRACT

A device for a rectoscope including a main pipe which is provided, at a first end portion, with a connection sub arranged to receive an optics head, and an elongated insertion portion, a second end portion being provided with a rectoscope mouth, and the center bore of the main pipe being arranged to receive an insertion cone, at least one fluid line being arranged in the main pipe, the fluid line extending from the first end portion to a second end portion of the main pipe.

7 Claims, 2 Drawing Sheets